United States Patent [19]

Tannenbaum

[11] 4,233,986
[45] Nov. 18, 1980

[54] APPARATUS AND METHOD FOR CONTROLLING PAIN BY TRANSCUTANEOUS ELECTRICAL STIMULATION (TES)

[75] Inventor: Joseph Tannenbaum, Jerusalem, Israel

[73] Assignee: Agar Ginosar Electronics and Metal Products, Doar Na Emek, Israel

[21] Appl. No.: 925,839

[22] Filed: Jul. 18, 1978

Related U.S. Application Data

[63] Continuation of Ser. No. 740,499, Nov. 10, 1976, abandoned.

[51] Int. Cl.$^3$ ............................................. A61N 1/36
[52] U.S. Cl. .................................................... 128/421
[58] Field of Search ............... 128/1 C, 419 R, 420 R, 128/421, 422, 423 R

[56] References Cited

U.S. PATENT DOCUMENTS

| | | | |
|---|---|---|---|
| 2,447,084 | 7/1949 | Rehman | 128/420 R |
| 2,498,882 | 2/1950 | Fizzell et al. | 128/421 |
| 2,700,975 | 2/1955 | Hopfinger et al. | 128/422 |
| 3,518,996 | 7/1970 | Cortinx | 128/422 |
| 3,794,022 | 2/1974 | Nowracaj et al. | 128/422 |
| 3,911,930 | 10/1975 | Hagfors et al. | 128/422 |
| 3,983,881 | 10/1976 | Wickham | 128/421 |
| 4,084,595 | 4/1978 | Miller | 128/422 |

FOREIGN PATENT DOCUMENTS 1365478  5/1964  France ....................... 128/1 C

*Primary Examiner*—William E. Kamm
*Attorney, Agent, or Firm*—Benjamin J. Barish

[57] ABSTRACT

Apparatus and method are described for controlling pain by transcutaneous electrical stimulation (TES), the apparatus comprising a pulse generator for generating periodic electrical pulses, skin electrodes coupled to the pulse generator and adapted to be placed in contact with the skin of the patient for applying the pulses thereto, and a pulse-width modulator for modulating the width of the pulses applied by the electrodes to the patient's skin. The skin electrodes include a survey electrode having a handle for moving it over the surface of the skin to locate the relevant nerve. The pulses applied are unsymmetrical, nearly square-shape, bipolar current pulses width-modulated 25–50% per period of 0.1 to 1.0 seconds.

10 Claims, 4 Drawing Figures

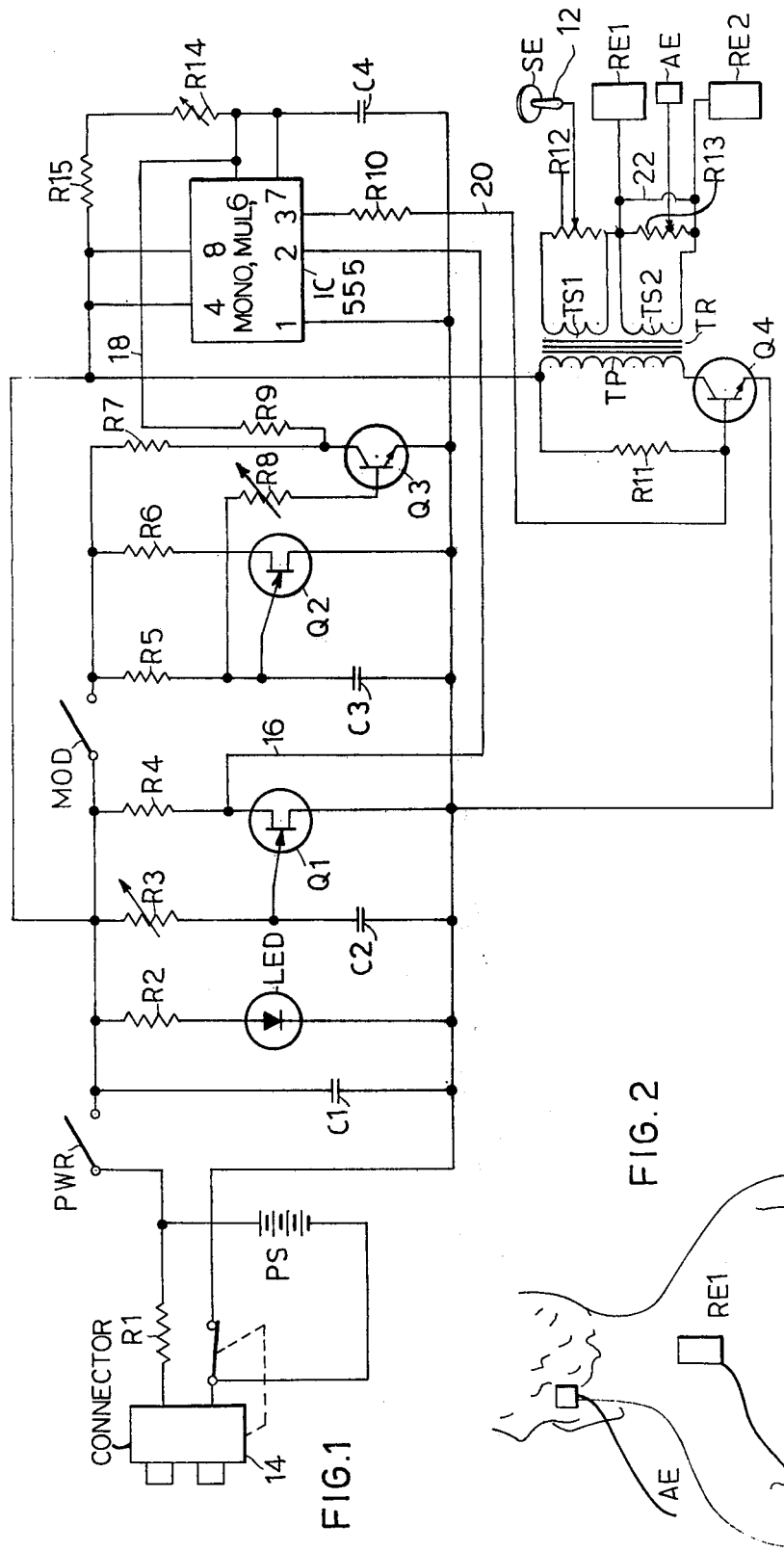

APPARATUS AND METHOD FOR CONTROLLING PAIN BY TRANSCUTANEOUS ELECTRICAL STIMULATION (TES)

RELATED APPLICATION

The present application is a continuation of my patent application Ser. No. 740,499, filed Nov. 10, 1976, now abandoned.

BACKGROUND OF THE INVENTION

The transcutaneous electrical stimulation (TES) treatment for controlling pain involves the application of periodic electrical pulses to the skin of the patient in the painful region. The equipment presently in use applies the pulses via skin electrodes coupled to a pulse generator which generates symmetrical (e.g. sine wave, square-wave, bell-shaped or triangular) pulses of fixed frequency and width. This treatment has been found effective to reduce pain in many (but not all) cases, and many theories have been proposed attempting to explain the mechanism of action by which it accomplishes this.

SUMMARY OF THE INVENTION

An object of the present invention is to provide apparatus and method to make the TES treatment even more effective for controlling pain.

According to a broad aspect of the invention, the TES treatment for controlling pain is made more effective by modulating the width (duration) of the pulses applied to the patient via the skin electrodes. It has been found that particularly good results can be obtained by modulating the width of the pulses 25–50% per period of 0.1 to 1.0 seconds, and by applying the pulses at a frequency of 50–150 Hz, a width of 68–740 microseconds, and a voltage of 60–150 volts.

Clinical data is set forth below showing that modulating the width of the pulses as described above increases the effectiveness of the TES treatment for reducing or aleviating pain. It is believed that the increased effectiveness of this treatment can be explained as follows: First, the width-modulation of the pulses prevents or decreases habituation to the stimulus. In addition, the width-modulated pulses are also believed to enhance muscle stimulation which increases the blood flow and decreases the local stagnant anoxia (a cause of pain) in the small blood vessels. The modulations activate the monosynaptic reflex and, in addition, produce a deep somatic and visceral effect which has a benefit in aleviating pain.

Further features and advantages of the invention will be apparent from the description below.

BRIEF DESCRIPTION OF THE DRAWINGS

The invention is herein described, by way of example only, with reference to the accompanying drawings, wherein:

FIG. 1 is a circuit diagram illustrating one form of apparatus constructed in accordance with the invention;

FIG. 2 is a schematic diagram illustrating the use of the apparatus of FIG. 1 in the TES treatment for controlling one form of headache pain;

FIG. 3 is a wave form diagram illustrating the width-modulated pulses produced by the apparatus of FIG. 1; and FIG. 4 illustrates an optional feature enabling the apparatus also to be used for intraneural pain control for anesthesia, instead of analgesia.

DESCRIPTION OF THE PREFERRED EMBODIMENT

The apparatus illustrated in FIG. 1 is basically a pulse generator having pulse-width modulating means for applying width-modulated pulses to a plurality of external skin electrodes which are to be applied to the skin of the patient in the painful region. In the apparatus of FIG. 1, the skin electrodes include two reference electrodes RE1, RE2 each having a relatively large surface area; an active electrode AE having a smaller surface area; and a survey electrode SE of even smaller surface area. The latter electrode has a handle 12 to facilitate its movement over the skin of the patient in order to locate the trigger point or the relevant nerve, as will be described more particularly below.

The pulse generator of FIG. 1 includes a chargeable battery PS as the power supply, the battery (e.g. 5–6 volts) being charged via a connector 14 and a resistor R1 (e.g. 68 ohms). The battery power supply is applied, via power switch PWR, filter capacitor C1 (100 ufd), and a light-emitting-diode indicator LED having a voltage-dropping resistor R2 (390 ohms) connected in series therewith, to a master oscillator circuit including a unijunction transistor Q1 (2N4871), variable resistor R3 (15 Kohms) another resistor R4 (390 ohms), and capacitor C2 (0.47 ufd). The output of the oscillator of transistor Q1 is applied via conductor 16 to Terminal-2 of an integrated circuit chip IC555 which acts as a one-shot monostable.

The power supply PS is also applied via modulator switch MOD to a modulator oscillator circuit including a second unijunction transistor Q2 (2N4871Q2), resistors R5 (15 Kohm) and R6 (680 ohm), and a capacitor C3 (4.7 ufd). The output of this oscillator circuit drives a transistor Q3 (2N4400) having a resistor R7 (3 Kohm) in its collector circuit connected to the power supply PS, and a base connected to the oscillator transistor Q2 via another variable resistor R8 (110 Kohm). The output of transistor Q3 is connected, via resistor R9 (3 Kohm) and conductor 18, to Terminal-6 of the integrated circuit chip IC55.

The output of integrated circuit chip IC555 is taken from its Terminal-3 and is applied via conductor 20 and resistor R10 (47 ohm) to the base of a further transistor Q4 (MJE 520) acting as a current amplifier. Its output is fed to the primary winding TP of a transformr TR connected across the collector of transistor Q4 and its base via resistor R11 (510 ohm). Transformer TR includes two secondary windings TS1, TS2, each connected at one side together via jumper wire 22, and to one of the reference electrodes RE1, RE2. The opposite side of transformer secondary winding TS1, is connected, via a voltage-divider resistor R12 (100 Kohm), to the survey electrode SE; and the opposite side of transformer secondary winding TS2 is connected, via voltage-divider resistor R13 (100 Kohm), to the active electrode AE.

IC555 is a well known integrated circuit chip, and therefore its specific construction and mode of operation are not described herein. When connected as illustrated in FIG. 1, with its Terminal-2 coupled to the output of the master oscillator circuit of transistor Q1, it acts as one-shot monostable multivibrator which is reset by the pulses from the master oscillator applied via conductor 16 to its Terminal-2. The frequency of the pulses is determined by the frequency of the master oscillator, which may be varied resistor R3. The width or duration of the pulses outputted by the one-shot monostable is determined by the pulses applied to its Terminal-6 via conductor 18 from transistor Q3 driven by the modulator oscillator circuit of transistor Q2; and the percent of modulation of this circuit may be varied by varying resistor R8. IC555 further includes resistors R14 (4.7 Kohm) and R15 (3 Kohm) connected between its Terminals 6,8 and 4, and capacitor C4 (0.47 ufd) connected between its Terminals 1, 7 and 6, as shown.

The provision of the two reference electrodes RE1, RE2, cooperable with the survey electrode SE and the active electrode AE, respectively, provides two separate channels for pain treatment. The reference electrodes RE1, RE2 are of large surface area, in this case being 15×5 cm, and are adapted to be placed on the skin at the part of the spinal column closest to the pain area. The active electrode AE is of smaller surface area, being in this case 3.5×2.5 cm, and is adapted to be placed on the skin at the painful region. Before using the active electrode AE, however, it is preferred to locate the painful area by the use of the survey electrode SE, which is of circular configuration 2 cm. in diameter, this electrode being provided with the handle 12 to facilitate its manipulation for locating the painful region.

All the electrodes are preferably made of vulcanized silicone rubber compound having an electrical resistance of 700 ohm/cm$^2$ and are preferably first coated with tap water or a conductive paste before application to the skin.

It will be appreciated that the output amplifier Q4 is a constant current amplifier as it has an output impedance many times higher than the interface resistance of the skin electrodes.

FIG. 2 illustrates the use of the apparatus for treating one form of headache, wherein one of the reference electrodes RE1 is placed at the top of the spinal column, and the active electrode AE is placed at the back of the head adjacent to the painful region.

FIG. 3 is a wave form diagram illustrating the train of width-modulated pulses produced by the pulse generator of FIG. 1. Thus, the pulses P1-Pn, outputted by the generator and applied by the skin electrodes to the patient, are of the same general shape but are width-modulated so that their widths continuously increase a predetermined percentage for a fixed period of modulation. In the waveforms illustrated in FIG. 3, the percentage of modulation is 25%, and the period of modulation is 0.2 seconds. Thus, the first pulse P1 has a width of 0.5 milli-seconds (i.e. 500 microseconds), the second pulse P2 10 milli-seconds thereafter has a pulse width of 0.5065 milli-seconds (506.5 microseconds), and the last pulse Pn 190 milliseconds after pulse P2 (i.e., 0.2 seconds from the start of the initial pulse P1) has a pulse width of 0.625 millseconds (625 microseconds).

It will be further seen from FIG. 3 that each of the pulses P1-Pn is unsymmetrical, bipolar, and nearly square-shaped. FIG. 3 shows the negative portion of the pulse waveform above the O-axis, since this is the more active phase. This pulse shape, resulting mainly from the reactance of the transformer TR, has a nearly square-shaped negative or polarising phase and an exponentially decaying positive or depolarising phase, and has been found to be more effective than the symmetrical or monopolar pulses heretofore used in TES treatment.

Preferably, the apparatus is first operated in the modulator-disable Mode, i.e. with the MOD switch open. After a predetermined time interval, for example 5–15 minutes of treatment, the MOD switch is closed to enable the modulator which effects the pulse-width modulation described above and illustrated in FIG. 3. 190 Ambulatory patients (107 men and 83 women, aged 16 to 80) suffering from various pain conditions, received the above-described TES treatment alone, or combined with other forms of pain therapy. All patients were referred by their treating physician with established diagnosis, each subsequently confirmed by clinical findings. Eighty five patients had tension-headache, migraine or post-traumatic headache; 27 had pain due to previous nerve injury or amputation; and 13 had herpes zoster. Of the latter, seven were treated in the acute phase (the first 3–5 weeks of the disease) while the others had long-standing post herpetic neuralgia. Of the remaining 65 patients, eight had severe localized pain due to bone metastases; nine had post-operative pain, namely chest pain after open heart surgery and thoracotomy, incisional pain after renal operation, mastectomy and plastic surgery; six were young, healthy athletes suffering from sudden muscle spasms in the legs; three had undergone chordotomy; and one had undergone thalamotomy. The rest of the patients were diagnosed as various forms of neuralgias, namely, meralgia paresthetica, trigeminal, intercostal and sciatic pain. These 65 patients also include three post C.V.A. with hemisparesis and pain in the affected arm, and two patients with pain in the foot after embolectomy.

The majority of the 190 patients had previously received various drugs for pain alleviation; they were directed to continue the same medication during the first T.E.S. sessions.

A trial of stimulation was initially given in order: (a) to find the optimal placement of the electrodes, e.g., to cover and concentrate the current stimulation over the affected area; and (b) to select a current strength that would give a comfortable vibrating sensation. The TES was administered for 20–30 minutes. After the first few minutes, there usually was habituation so the stimulus could be increased without discomfort, even to a point where sometimes muscle contractions followed. The treatment was repeated 2–3 times weekly up to about 10 sessions, depending on the therapeutic progress. If effective (the patient's subjective evaluation being the most important guide), the TES was continued either in the hospital or at home by self-administration.

Switch MOD was closed to produce pulse-width modulation during the TES treatment after adequate current had been reached. The current activated by the pulse modulation prevents habituation to the stimulus as described above, and thus obviates the need of changing of the current intensity during treatment. In addition, the pulse modulation is also effective as a muscle stimulator as described above.

With two electrodes of the same size, the current density beneath each of them is equal. Whenever stimulation of local skin receptors is intended, two electrodes of the same size should therefore be used. If the pain is diffuse and spread over a large area, the two big electrodes RE1, RE2 are applied. With two electrodes of unequal size, the current density under the small electrode (e.g. AE or SE) is higher than under the large one (RE1 and RE2). When stimulation of trigger points or of an accessible superficial nerve is the treatment of choice, a large (e.g. RE1) and a small (e.g. AE) electrode should be used. The two electrodes are placed at a distance of 5-30 cm from one another, depending on the localization of the pain.

To assess the effects of the TES treatment, a pain profile and scoring system was determined before the treatment, and repeated after a series of sessions. This profile included (1) pain intensity; (2) pain duration and its frequency; (3) degree of medication; (4) limitation of movement; (5) daily activity level; (6) mood. Each feature was given a score between 0-4 (4 being the more severe condition), the total score being 24. The results were classified as "moderate" if pain relief was obtained only during the TES treatment or if the scoring decreased up to four points. The results were considered "good" if pain relief was obtained for various periods after treatment and the initial scoring was reduced by 6-8 points. It must be noted that the results represent the effect during a series of treatment, and long-term follow-up was not available in most patients.

Good effects were obtained in 50.6% of the patients, moderate in 27.8%, and no effect in 21.6%. There is no significant overall difference between the various groups, except for herpes zoster with 38.5% "good" results (five out of 13 patients; these five patients were all the acute stage).

Although there were only a small number of patients in each sub-group, and many individual variations were seen, some cases are worthy of comment. Two aged patients with hemiparesis and two after embolectomy had good results with the TES treatment and continued the treatment at home. (The importance of a non-invasive prolonged method of treatment in elderly patients suffering from severe systemic diseases and in whom a number of drugs are contraindicated or ineffective, is obvious). The same was true in one patient with sternal pain after surgery for double valve replacement, and two others with severe metastatic pain. The latter operated the stimulator continuously during the day. A number of patients activated the stimulation to the point where it elicited muscle contractions. The results were poor in trigeminal neuralgia and facial pain.

If effective at all, the pain generally diminished soon after the application of the current. Thus, if there is no effect during the first few sessions, treatment may be discontinued. However, it should not be stopped before it has been ascertained that the painful area has been well covered by the stimulation.

Some patients returned to the clinic every few months for repeated TES sessions. Since the introduction of this treatment, the number of nerve blocks appreciably decreased. It seems that when TES and nerve blocks were combined, the patient could be easier weaned from the blocks. In other instances, where nerve blocks were considered, but TES was applied first as a trial treatment, blocks became superfluous. The treatment had no side effects even after prolonged application.

While the invention has been described above with respect to one preferred embodiment, it will be appreciated that many variations may be made. For example, the frequency of application of the pulses may generally be varied from 50-150 Hz, the apparatus described above operating at a frequency of 90 Hz. In addition, the pulse width may be from 68-740 microseconds, the apparatus described above producing pulses of a width of 500 microseconds. The pulse voltage may generally be from 60-150 volts, 90 volts having been found most effective in the above apparatus. The current peak of the pulses depends on the pulse width; thus, pulses having a width of 68 microseconds preferably should have a peak of about 60 milliamps, and pulses having a width of 740 microseconds preferably should have a peak of about 15 milliamps. The apparatus described above operates at a pulse width of 500 microseconds and a peak of 20 milliamps. The modulation period may generally vary from 100 milliseconds (0.1 second) to 1000 milliseconds (1 second), the preferred example described above having a modulation period of 0.2 seconds. The modulation percentage may vary from 25-50% per period, the preferred modulation being 25% in the example described above.

While the invention has been found particularly effective in the TES treatment for controlling pain, it will be appreciated that it could also be used as a muscle stimulator since it has a muscle stimulating effect as described above.

Further, the optional attachment illustrated in FIG. 4 may also be included to provide a capability of producing anesthesia in addition to analgesia. The unit of FIG. 4 is adapted to be plugged into terminals TAE and TREI, respectively, of FIG. 1 to produce a voltage between a needle electrode NE and a skin electrode $AE^1$ of the size of electrode AE in FIG. 1. The needle electrode in this case receives positive potential and is adapted to penetrate the skin and to be inserted into the nerve anesthesized. The needle is insulated except for the tip which is bare. The potential applied to the nerve by needle electrode NE is derived across the plugged-in terminals TAE and TREI via resistors R20 (100 Kohm), R21 (10 Kohm), and R22 (10 Kohm), which together divide, by 5-10, the voltage applied between electrodes NE and $AE^1$. The circuit further includes a diode D20 which limits the negative phase of the pulse. The use of width-modulated pulses for anesthesia has also been found advantageous in that it requires less average energy than non-modulated pulses.

Many other variations, modifications and applications of the invention will be apparent.

What is claimed is:

1. Apparatus for controlling pain in a patient by transcutaneous electrical stimulation comprising: a pulse generator for continuously generating periodic electrical pulses of a width of from 68 to 740 microseconds, and a voltage of from 60 to 150 volts; external electrode means including at least a pair of skin electrodes coupled to said pulse generator and adapted to be placed in contact with the skin of the patient for applying said pulses thereto; and a pulse-width modulator for modulating the width of the pulses generated by said generator and applied by said electrodes to the patient's skin.

2. Apparatus according to claim 1, wherein said pulse generator generates said pulses at a frequency of 50-150 Hz, and wherein said pulse-width modulator modulates the pulse width 25-50% per period of 0.1 to 1.0 seconds.

3. Apparatus according to claim 2, wherein said frequency is about 90 Hz, said pulse width is about 500 microseconds, said voltage is about 90 volts, said modulation is about 25%, and said modulation period is about 0.2 seconds.

4. Apparatus according to claim 1, further including a Mode switch for selectively disabling and enabling said pulse-width modulator.

5. Apparatus according to claim 1, wherein said pulse generator includes a constant current amplifier having an output impedance many times higher than the interface resistance of said skin electrodes.

6. Apparatus according to claim 5, wherein the pulses generated by said pulse generator are unsymmetrical, nearly square-shape, bipolar current pulses.

7. Apparatus according to claim 1, wherein said pulse generator includes a first oscillator for generating pulses at a fixed frequency and width, and a one-shot monostable multivibrator connected to receive said pulses from the first oscillator and producing output pulses at the frequency thereof, and wherein said pulse width modulator comprises a second oscillator generating further pulses applied to said one-shot monostable multivibrator and effective to modulate the width of said output pulses thereof in accordance with the frequency of the second oscillator.

8. A method for controlling pain in a patient by transcutaneous electrical stimulation comprising the steps of continuously generating width-modulated pulses and continuously applying same to the skin of the patient via a pair of skin electrodes placed in contact with the skin of the patient, said width-modulated pulses being applied of a width of from 68 to 740 microseconds and a voltage of from 60 to 150 volts.

9. The method according to claim 8, wherein said pulse-width-modulated pulses are applied at a frequency of 50–150 Hz, and are modulated 25–50% per period of 0.1 to 1.0 seconds.

10. The method according to claim 8, wherein the pulses applied to the skin are unsymmetrical, nearly square-shape, bipolar current pulses.

* * * * *